United States Patent
Anderson-Taylor et al.

[11] Patent Number: 5,837,652
[45] Date of Patent: Nov. 17, 1998

[54] HERBICIDAL COMPOSITIONS

[75] Inventors: Gordon Anderson-Taylor, Ongar, England; Stephen Malcolm Irons, Lincoln, Nebr.; Brian Malcolm Luscombe; Alan Gamblin, both of Ongar, England

[73] Assignee: Rhone-Poulenc Agriculture Limited, Essex, England

[21] Appl. No.: 766,182

[22] Filed: Dec. 12, 1996

Related U.S. Application Data

[60] Provisional application No. 60/008,912, Dec. 20, 1995.
[51] Int. Cl.$^6$ .......................... A01N 37/34; A01N 43/36
[52] U.S. Cl. ........................................... 504/138; 504/141
[58] Field of Search ..................................... 504/138, 141

[56] References Cited

U.S. PATENT DOCUMENTS

| | | | |
|---|---|---|---|
| 5,222,595 | 6/1993 | Gouge et al. | 206/205 |
| 5,224,601 | 7/1993 | Gouge et al. | 206/524.7 |
| 5,323,906 | 6/1994 | Gouge et al. | 206/524.7 |
| 5,351,831 | 10/1994 | Gouge et al. | 206/524.7 |
| 5,416,061 | 5/1995 | Hewett et al. | 504/141 |

FOREIGN PATENT DOCUMENTS

| | | |
|---|---|---|
| 0418175 | 3/1991 | European Pat. Off. . |
| 0487357 | 5/1992 | European Pat. Off. . |
| 0527036 | 2/1993 | European Pat. Off. . |
| 0560482 | 9/1993 | European Pat. Off. . |
| 0577702 | 1/1994 | European Pat. Off. . |
| 0580439 | 1/1994 | European Pat. Off. . |
| 0609797 | 8/1994 | European Pat. Off. . |
| 0609798 | 8/1994 | European Pat. Off. . |
| 2675340 | 10/1992 | France . |
| 2284547 | 6/1995 | United Kingdom . |
| 94/14782 | 7/1994 | WIPO . |
| 94/18179 | 8/1994 | WIPO . |

OTHER PUBLICATIONS

*Chemical Abstracts*, vol. 110, No. 17, abstract No. 149835 (Apr. 24, 1989).
Worthing et al, "The Pesticide Manual" 9th Ed. pp. 100–102.
Tammes, *Netherlands Journal of Plant Pathology*, 70, pp. 73–80 (1964).
Limpel et al, *1. Proc. NEWCC 16*, pp. 48–53 (1962).
Luscombe et al, *Proc. N. Cert. Weed Sci. Soc.*, 49, 57–58 (1994).
Colby, *Weeds* 15, pp. 20–22 (1967).

*Primary Examiner*—Allen J. Robinson
*Attorney, Agent, or Firm*—Burns, Doane, Swecker & Mathis, L.L.P.

[57] ABSTRACT

The invention relates to a composition comprising
(a) a 4-benzoylisoxazole herbicide; and
(b) bromoxynil or ioxynil, or an agriculturally acceptable salt or ester thereof, or a mixture thereof;
and to the use of this composition in controlling the growth of weeds.

18 Claims, 3 Drawing Sheets

HERBICIDAL COMPOSITIONS

CROSS-REFERENCE TO RELATED APPLICATION

This application claims the priority of U.S. provisional patent application Ser. No. 60/008,912, filed Dec. 20, 1995, incorporated by reference herein in its entirety and relied upon.

BACKGROUND OF THE INVENTION

1. Field of the Invention

The present invention relates to a method of controlling the growth of weeds by the application of hydroxybenzonitrile herbicides such as bromoxynil or ioxynil, or agriculturally acceptable salts or esters thereof, and certain 4-benzoylisoxazoles, and to compositions containing them.

2. Description of the Related Art

Bromoxynil(3,5-dibromo-4-hydroxybenzonitrile) and ioxynil(4-hydroxy-3,5-diiodobenzonitrile) are known as "HBN" (hydroxybenzonitrile) herbicides and may be used for post-emergence weed control in maize, wheat and barley. Although giving control of a wide range of broad-leaf weeds, control of some important species, for example *Amaranthus retroflexus, Ipomoea purpurea, Stellaria media*, and *Viola arvensis* is unreliable. Owing to a lack of residual activity in the soil, HBN herbicides do not control the weeds which emerge after application. Bromoxynil and ioxynil have no useful activity against grass or sedge weeds.

It is to be understood that where in this specification reference is made to "HBN herbicides" it is intended to refer, where the context so permits, to bromoxynil or ioxynil in the form of the parent phenol (acid equivalent: a.e.), an agriculturally acceptable salt or ester thereof, preferably an agriculturally acceptable metal or amine salt, or an agriculturally acceptable ester thereof with an alkanoic acid having from 2 to 10 carbon atoms, or to mixtures thereof.

4-Benzoylisoxazoles are known from the literature; see, for example, European Patent Publications Nos. 0418175, 0487357, 0527036, 0560482, 0580439, 0609797 and 0609798; and WO94/14782 and WO94/18179, all of which are incorporated by reference herein in their entireties and relied upon. Also, the compound 5-cyclopropyl-4-(2-methylsulfonyl-4-trifluoromethylbenzoyl)isoxazole has been disclosed as giving good pre-emergence control of grasses and broad-leaved weeds in maize (Vrabel et al; Proc. N. Cert. Weed Sci. Soc., 1994, 49). The use of this compound in post-emergence treatments is not however discussed.

As a result of research and experimentation it has now been discovered that the use of certain 4-benzoylisoxazole derivatives in combination with HBN herbicides add to their capabilities of controlling a wide spectrum of broad-leaf weeds, grasses and sedges by both foliar activity and residual soil activity.

In addition to this it has been found that the combined herbicidal activity of combinations of 4-benzoylisoxazole derivatives with HBN herbicides against certain species is greater than expected when applied pre- or preferably post-emergence (e.g. as a post-emergence spray), i.e. the herbicidal activity of combinations of 4-benzoylisoxazole derivatives with HBN herbicides, e.g. bromoxynil, showed an unexpected degree of synergism, as defined either by P. M. L. Tammes, Netherlands Journal of Plant Pathology, 70 (1964), pp 73–80 in a paper entitled "Isoboles, a graphic representation of synergism in pesticides"; or by Limpel, L. E., P. H. Schuldt and D. Lamont, 1962, 1. Proc. NEWCC 16, 48–53 using the formula:

$$E = X + Y - \frac{X \cdot Y}{100}$$

also known as the Colby formula (Colby S. R., 1967, Weeds 15, 20–22), where:

E=the expected percent inhibition of growth by a mixture of two herbicides A and B at defined doses.

X=the percent inhibition of growth by herbicide A at a defined dose.

Y=the percent inhibition of growth by herbicide B at a defined dose.

When the observed percentage of inhibition by the mixture is greater than the expected value E using the formula above the combination is synergistic.

The unexpected synergistic effect gives improved reliability of control of a number of weed species and allows for a reduction in the amount of active ingredients employed.

A high level of control of these weeds is desirable to prevent:

1) yield loss, through competition and/or difficulties with harvest,
2) crop contamination leading to storage and cleaning difficulties, and
3) unacceptable weed seed return to the soil.

SUMMARY OF THE INVENTION

Accordingly the present invention provides a method for the control of the growth of weeds at a locus which comprises applying to the locus a herbicidally effective amount of:

(a) a 4-benzoylisoxazole herbicide; and
(b) bromoxynil or ioxynil or an agriculturally acceptable salt or ester thereof, preferably a metal or amine salt or an ester thereof with an alkanoic acid having from 2 to 10 carbon atoms.

For this purpose, the 4-benzoylisoxazole herbicide and HBN herbicide are normally used in the form of herbicidal compositions (i.e. in association with compatible diluents or carriers and/or surface-active agents suitable for use in herbicidal compositions), for example as hereinafter described.

DESCRIPTION OF PREFERRED EMBODIMENTS

Preferably the 4-benzoylisoxazole is of formula (I):

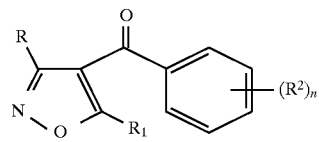

wherein:

R is hydrogen or —$CO_2R^3$;

$R^1$ is cyclopropyl;

$R^2$ is selected from halogen (preferably chlorine or bromine), —$S(O)_p$Me and $C_{1-6}$ alkyl or haloalkyl (preferably trifluoromethyl);

n is two or three;

p is zero, one or two; and $R^3$ is $C_{1-4}$ alkyl.

In formula (I) above, compounds in which n is three and the groups $(R^2)_n$ occupy the 2, 3 and 4-positions of the benzoyl ring; or in which n is two and the groups $(R^2)_n$ occupy the 2- and 4-positions of the benzoyl ring are preferred.

In formula (I) above, preferably one of the groups $R^2$ is —$S(O)_p$Me.

The 4-benzoylisoxazoles of particular interest in combination with HBN herbicides include the following:

A  5-cyclopropyl-4-(2-methylsulfonyl-4-trifluoromethyl) benzoylisoxazole;

B  5-cyclopropyl-4-(4-methylsulfonyl-2-trifluoromethyl) benzoylisoxazole;

C  4-(2-chloro-4-methylsulfonyl)benzoyl-5-cyclopropylisoxazole;

D  4-(4-chloro-2-methylsulfonyl)benzoyl-5-cyclopropylisoxazole;

E  4-(4-bromo-2-methylsulfonyl)benzoyl-5-cyclopropylisoxazole;

F  ethyl 3-[5-cyclopropyl-4-(3,4-dichloro-2-methylsulfenyl)benzoylisoxazole]carboxylate;

G  5-cyclopropyl-4-(3,4-dichloro-2-methylsulfonyl) benzoylisoxazole; and

H  ethyl 3-[5-cyclopropyl-4-(2-methylsulfonyl-4-trifluoromethyl)benzoylisoxazole]carboxylate.

Of these, compounds A, F and H are preferred, especially Compounds A and F.

The HBN herbicide is preferably present as either the parent phenol or as an ester, most preferably selected from the butyrate, heptanoate and octanoate or mixtures thereof.

The amounts of the 4-benzoylisoxazole herbicide and HBN herbicide applied vary with the nature of the weeds, the compositions used, the time of application, the climatic and edaphic conditions and (when used to control the growth of weeds in crop-growing areas) the nature of the crops. When applied to a crop-growing area, the rate of application should be sufficient to control the growth of weeds without causing substantial permanent damage to the crop. In general, taking these factors into account, application rates of from about 5 g to about 500 g of the 4-benzoylisoxazole herbicide and from about 30 g to about 600 g a.e. of HBN herbicide per hectare give good results. However, it is to be understood that higher or lower application rates may be used, depending upon the particular problem of weed control encountered.

The 4-benzoylisoxazole herbicide and HBN herbicide in combination may be used to control selectively the growth of weeds, for example to control the growth of those species hereinafter mentioned, by pre- or preferably post-emergence application in a directional or non-directional fashion, e.g. by directional or non-directional spraying, to a locus of weed infestation which is an area used, or to be used, for growing crops, for example wheat, barley, oats, rye, maize and rice, soya beans, field and dwarf beans, peas, lucerne, cotton, peanuts, flax, onions, carrots, oilseed rape, sunflower, sugarcane, potatoes and permanent or sown grassland before or after sowing of the crop or before or after emergence of the crop.

For the selective control of weeds at a locus of weed infestation which is an area used, or to be used, for the growing of crops, application rates of from about 5 g to about 500 g of the 4-benzoylisoxazole and from about 30 g to about 360 g a.e. of HBN herbicide per hectare are particularly suitable, more preferably from about 20 to about 300 g of the 4-benzoylisoxazole herbicide and from about 60 g to about 200 g a.e. of HBN herbicide per hectare.

The use of the 4-benzoylisoxazole herbicide and HBN herbicide for the control of weeds in maize, winter or spring cereals, or sugarcane is preferred.

Where the 4-benzoylisoxazole is Compound A, the HBN herbicide is bromoxynil and the mixture is for use in maize, application rates of from about 5 to about 75 g per hectare of the 4-benzoylisoxazole and from about 20 g to about 280 g a.e. per hectare of bromoxynil are preferred, more preferably from about 10 to about 50 g of 4-benzoylisoxazole and from about 35 g to about 280 g a.e. of bromoxynil per hectare, even more preferably from about 15 to about 25 g of 4-benzoylisoxazole and about 140 g a.e. of bromoxynil per hectare.

Where the 4-benzoylisoxazole is Compound A, the HBN herbicide is bromoxynil and the mixture is for use in spring cereals, application rates of from about 5 to about 100 g per hectare of the 4-benzoylisoxazole herbicide and from about 30 g to about 280 g a.e. per hectare of bromoxynil are preferred, more preferably from about 10 to about 60 g of 4-benzoylisoxazole and from about 60 g to about 280 g a.e. of bromoxynil per hectare, even more preferably from about 20 to about 40 g of 4-benzoylisoxazole and about 120 g a.e. of bromoxynil per hectare.

Where the 4-benzoylisoxazole is Compound A, the HBN herbicide is bromoxynil and the mixture is for use in winter cereals, application rates of from about 10 to about 150 g per hectare of the 4-benzoylisoxazole and from about 60 g to about 360 g a.e. per hectare of bromoxynil are preferred, more preferably from about 10 to about 60 g of the 4-benzoylisoxazole and from about 80 g to about 280 g a.e. of bromoxynil per hectare, even more preferably from about 20 to about 40 g of 4-benzoylisoxazole and about 120 g a.e. of bromoxynil per hectare.

Where the 4-benzoylisoxazole is Compound F and the HBN herbicide is bromoxynil, the mixture is most preferably used in controlling weeds found in maize. In this use, application rates of from about 25 to about 300 g per hectare of the 4-benzoylisoxazole and from about 60 to about 120 g a.e. per hectare of bromoxynil are preferred, more preferably from 150 to 250 g per hectare of the 4-benzoylisoxazole herbicide and about 120 g a.e. of bromoxynil.

Where the HBN herbicide is ioxynil, the mixture is preferably used to control weeds found in cereal crops such as wheat and barley (in particular, winter wheat and winter barley). The ioxynil is preferably used in the form of an ester, preferably the octanoate ester.

The mixtures of the present invention may also be used to control the growth of weeds at loci which are not crop-growing areas but in which the control of weeds is nevertheless desirable. Examples of such non-crop-growing areas include airfields, industrial sites, railways, roadside verges, the verges of rivers, irrigation and other waterways, scrublands and fallow or uncultivated land, in particular where it is desired to control the growth of weeds in order to reduce fire risks. When used for such purposes in which a total herbicidal effect is frequently desired, the active compounds are normally applied at dosage rates higher than those used in crop-growing areas as hereinbefore described. The precise dosage will depend upon the nature of the vegetation treated and the effect sought. In general, application rates of from about 125 g to about 500 g per hectare of the 4-benzoylisoxazole herbicide and from about 30 g to about 600 g a.e. per hectare of HBN herbicide are used, more preferably from about 150 g to about 250 g of the 4-benzoylisoxazole herbicide and from about 60 to about 280 g a.e. per hectare of HBN herbicide.

Figure 1:
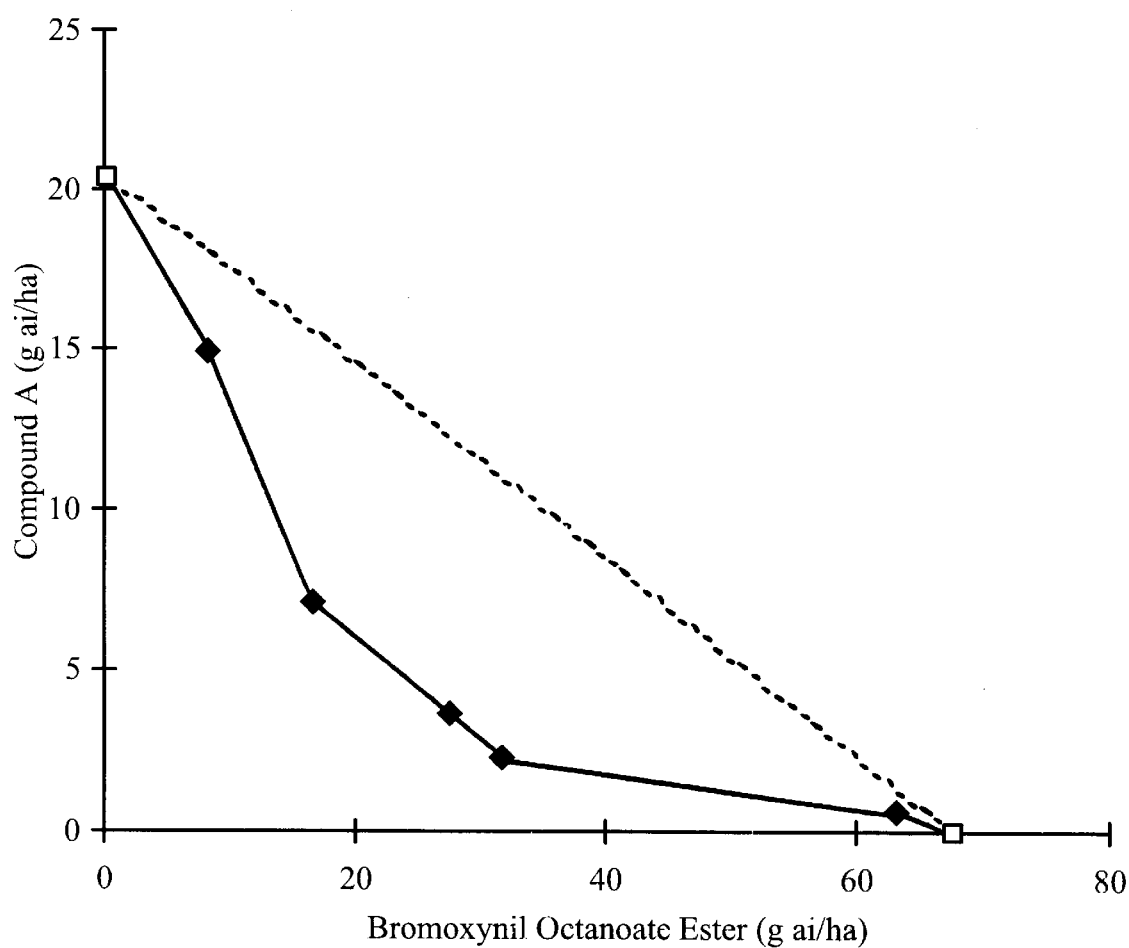
FIG. 1 is an ED50 plot calculated from observed values (-●-) and a corresponding plot of expected additive values (dashed line) for the mixtures of Compound A with bromoxynil against the weed species *Galium aparine*.

The following non-limiting examples illustrate the method of the invention. Unless otherwise specified, in the examples the application rates for the HBN herbicides refer to the amount of active ingredient present. In the description that follows the following Bayer codes are used for the various weed and crop species:

| Bayer Code | Species | Bayer Code | Species |
|---|---|---|---|
| GALAP | *Galium aparine* | ABUTH | *Abutilon threophrasti* |
| VERHE | *Veronica hederifolia* | AMARE | *Amaranthus retroflexus* |
| VIOAR | *Viola arvensis* | AMATA | *Amaranthus sp* |
| STEME | *Stellaria media* | SETFA | *Setaria faberi* |
| MATCH | *Matricaria chamomilla* | SETLU | *Setaria lutescens* |
| FUMOF | *Fumaria officinalis* | SORVU | *Sorghum vulgare* |
| MATSS | *Matricaria spp.* | SORHA | *Sorghum halepense* |
| PAPRH | *Papaver rhoeas* | CASOB | *Cassia obtusifolia* |
| SINAR | *Sinapis arvensis* | SIDSP | *Sida spinosa* |
| PANI | *Panicum dichotomiflorum* | LAMAM | *Lamium amplexicaule* |
|  |  | TRAW | *Triticum aestrium* |

EXAMPLE 1

The following field trials were conducted post-emergence of the weed and crop species at a research farm in Nebraska, U.S.A. (a silt loam soil; pH 7.0; content 18% sand; 56% silt and 26% clay). Compound A (formulated as a wettable powder) and bromoxynil (as the commercially available emulsifiable concentrate "Buctril 2EC"™, the octanoate ester) were dissolved in water and applied either alone or in mixtures to approximately 7 square meter plots at a spray volume rate of from 100 to 300 liters/ha. The crop and weed species had been drill sown 27 days earlier. Three replicates were performed and the percentage phytotoxicity was assessed visually 35 days after treatment in comparison with an untreated control.

In the tables that follow, the figure in parentheses represents the expected percentage level of control according to the Colby formula.

RESULTS

TABLE A1

*Setaria faberi*

| | | Bromoxynil | |
|---|---|---|---|
| | Dose (g/ha) | 0 | 210 |
| Compound A | 0 | — | 17 |
| | 12.5 | 20 | 65(34) |
| | 25 | 40 | 89(50) |
| | 50 | 77 | 98(81) |

TABLE A2

*Digitaria sanguinalis*

| | | Bromoxynil | |
|---|---|---|---|
| | Dose (g/ha) | 0 | 210 |
| Compound A | 0 | — | 20 |
| | 12.5 | 20 | 83(36) |
| | 25 | 63 | 100(70) |
| | 50 | 93 | 100(94) |

TABLE A3

*Setaria viridis*

| | | Bromoxynil | |
|---|---|---|---|
| | Dose (g/ha) | 0 | 210 |
| Compound A | 0 | — | 27 |
| | 12.5 | 27 | 62(47) |
| | 25 | 40 | 87(56) |
| | 50 | 78 | 88(84) |

TABLE A4

*Panicum dichotomiflorum*

| | | Bromoxynil | |
|---|---|---|---|
| | Dose (g/ha) | 0 | 210 |
| Compound A | 0 | — | 23 |
| | 12.5 | 30 | 68(46) |
| | 25 | 50 | 100(62) |
| | 50 | 78 | 100(83) |

TABLE A5

*Echinochloa crus-galli*

| | | Bromoxynil | |
|---|---|---|---|
| | Dose (g/ha) | 0 | 210 |
| Compound A | 0 | — | 17 |
| | 12.5 | 33 | 93(44) |
| | 25 | 78 | 100(82) |
| | 50 | 100 | 100(100) |

TABLE A6

*Sorghum vulgare*

| | | Bromoxynil | |
|---|---|---|---|
| | Dose (g/ha) | 0 | 210 |
| Compound A | 0 | — | 16 |
| | 12.5 | 27 | 57(39) |
| | 25 | 40 | 90(50) |
| | 50 | 78 | 98(82) |

TABLE A7

*Setaria glauca*

| | | Bromoxynil | |
|---|---|---|---|
| | Dose (g/ha) | 0 | 210 |
| Compound A | 0 | — | 17 |
| | 12.5 | 27 | 53(39) |
| | 25 | 38 | 88(49) |
| | 50 | 73 | 88(78) |

TABLE A8

Maize (*Zea Mays*: variety: PIONEER 3394)

| | | Bromoxynil | |
|---|---|---|---|
| | Dose (g/ha) | 0 | 210 |
| Compound A | 0 | — | 0 |
| | 12.5 | 0 | 0(0) |
| | 25 | 0 | 5(0) |
| | '50 | 0 | 8(0) |

EXAMPLE 2

The following glasshouse experiments were conducted to determine the efficacy of Compound F with bromoxynil as described below.

Compound F was formulated as a 50% wettable powder containing the following ingredients:

| Compound F | 50% |
|---|---|
| Arylan SX flake | 3% |
| Arkopon T | 5% |
| Sopropon T36 | 1% |
| Tixosil 38 | 3% |
| China Clay | 38% |

It was dissolved in water in the presence of 0.1% "Agral"™ (an alkyl phenol ethoxylate) and applied post-emergence on the weed species. Bromoxynil (as the commercial formulation "Pardner"™ at 225 g/l) was dissolved in water, also in the presence of 0.1% "Agral"™ and applied in the same manner at various application rates. Additionally the combination was tank mixed. The spray jet and pressure used to apply the compounds gave a volume equivalent to 290 l/ha. Treatment effects were assessed visually about 14 days after treatment. In addition "Agral"™ was applied on its own to determine its intrinsic phytotoxicity. The weeds were at the following growth stage when treated:

| Code | Species | Stage at treatment |
|---|---|---|
| CASOB | *Cassia obtusifolia* | cots - 1 leaf |
| SIDSP | *Sida spinosa* | cots - 2 leaf |
| CYPES | *Cyperus esculentus* | 4–5 leaf |
| DIGSA | *Digitaria sanguinalis* | 2–3 leaf |
| ECHCG | *Echinochloa crus-galli* | 3 leaf |
| PANDI | *Panicum dichotomifluorum* | 3 leaf |
| SETFA | *Setaria faberi* | 2–3 leaf |
| SETVI | *Setaria viridis* | 3 leaf |
| SORHA | *Sorghum halepense* | 3 leaf |

In the Tables that follow, "Brom" means bromoxynil as described above. The figures in parentheses indicate the expected level of weed control according to the Colby formula.

TABLE B1

| Compound | Rate (g/ha) | CASOB | SIDSP | CYPES | DIGSA | ECHCG | PANDI | SETFA | SETVI | SORHA |
|---|---|---|---|---|---|---|---|---|---|---|
| F(+0.1% Agral) | 16 | 50 | 50 | 0 | 40 | 90 | 30 | 80 | 0 | 80 |
| | 32 | 70 | 60 | 20 | 50 | 95 | 50 | 90 | 30 | 95 |
| | 63 | 80 | 70 | 20 | 70 | 95 | 60 | 100 | 60 | 100 |
| | 125 | 85 | 70 | 30 | 85 | 100 | 90 | 100 | 80 | 100 |
| Bromoxynil (+0.1% Agral) (BROM) | 63 | 0 | 50 | 0 | 0 | 0 | 0 | 0 | 10 | 0 |
| | 125 | 30 | 60 | 0 | 20 | 20 | 0 | 10 | 30 | 0 |
| | 250 | 40 | 60 | 0 | 30 | 20 | 0 | 30 | 30 | 20 |
| F + BROM | 16 + 63 | 85(50) | 80(75) | 10(0) | 60(52) | 100(90) | 60(30) | 90(80) | 30(10) | 95(80) |
| F + BROM | 32 + 63 | 100(70) | 100(80) | 20(20) | 60(60) | 100(95) | 70(50) | 90(90) | 70(37) | 95(95) |
| F + BROM | 63 + 63 | 90(80) | 90(85) | 40(20) | 80(76) | 100(95) | 70(60) | 100(100) | 80(64) | 100(100) |
| F + BROM | 125 + 63 | 90(85) | 90(85) | 40(30) | 85(88) | 100(100) | 85(90) | 100(100) | 100(82) | 100(100) |
| F + BROM | 16 + 125 | 90(65) | 85(80) | 20(0) | 60(58) | 100(92) | 20(30) | 100(82) | 66(30) | 100(80) |
| F + BROM | 32 + 125 | 80(79) | 100(84) | 20(20) | 70(65) | 100(96) | 70(50) | 100(91) | 70(51) | 100(95) |
| F + BROM | 63 + 125 | 70(86) | 90(88) | 30(20) | 85(79) | 100(96) | 90(60) | 100(100) | 100(72) | 100(100) |
| F + BROM | 125 + 125 | 70(90) | 90(88) | 50(30) | 100(90) | 100(100) | 90(90) | 100(100) | 100(86) | 100(100) |
| F + BROM | 16 + 250 | 80(70) | 80(80) | 10(0) | 60(64) | 100(92) | 50(30) | 100(86) | 80(30) | 95(84) |
| F + BROM | 32 + 250 | 80(82) | 100(84) | 30(20) | 80(70) | 100(96) | 80(50) | 100(93) | 95(51) | 100(96) |
| F + BROM | 63 + 250 | 90(88) | 100(88) | 40(20) | 100(82) | 100(96) | 90(60) | 100(100) | 95(72) | 100(100) |
| F + BROM | 125 + 250 | 70(91) | 100(88) | 70(30) | 100(91) | 100(100) | 90(90) | 100(100) | 95(86) | 100(100) |
| 0.1% Agral | — | 0 | 0 | 0 | 0 | 0 | 0 | 0 | 0 | 0 |

EXAMPLE 3

The following field trial was conducted to establish the efficacy of the mixtures of the invention in winter cereals. The trial was conducted in New Jersey post emergence of the weed and crop species. Compound A (formulated as a 75% wettable granule) and bromoxynil (commercial emulsifiable concentrate formulation "Buctril"™, containing 240 g/l of the octanoate ester) were dissolved in water and applied either alone or in tank mixes of various application rates to 3 meters by 5 meters plots (sandy loam soil) in which had been sown six months earlier the weed and crop species. The spray rate was 300 l/ha and 3 replicates were performed. The phytotoxicity was assessed 35 days after treatment and at the time of treatment the growth stage of the plants was as follows:

| Code | Species | Growth Stage (Height) |
|---|---|---|
| LAMAM | Lamium amplexicaule | 10–15 cm |
| STEME | Stellaria media | 18–20 cm |
| TRAW | Triticum aestrium (Variety: Pioneer 2548) | 20–25 cm |

The results are shown in the table that follows (N/D means no data available; "Brom" refers to the bromoxynil described above).

Results

TABLE C1

| Compound | Rate (g/ha) | WEED LAMAM | STEME | CROP TRAW |
|---|---|---|---|---|
| A | 10 | 55 | 65 | 0 |
| A | 20 | 47 | 47 | 0 |
| A | 40 | 78 | 83 | 0 |
| Brom | 60 | 23 | 20 | 0 |
| Brom | 120 | 17 | 23 | 0 |
| A + Brom | 10 + 60 | 83(65) | 82(72) | 0 |
| A + Brom | 10 + 120 | 68(63) | 75(73) | 0 |
| A + Brom | 20 + 60 | 80(59) | 78(58) | 0 |
| A + Brom | 20 + 120 | 93(56) | 88(59) | 0 |
| A + Brom | 40 + 60 | 88(83) | 78(86) | 0 |
| A + Brom | 40 + 120 | 93(82) | 92(87) | 0 |

EXAMPLE 4

The following glasshouse experiments were conducted to determine the efficacy of mixtures of Compound A and bromoxynil.

Compound A (technical material) and bromoxynil (octanoate ester, technical material) were dissolved in acetone and made up in water. Treatments were applied of the compounds alone and in tank mixes. The test solutions were applied post-emergence to the plants at a spray rate of 290 liters/ha. Four replicates were performed and the pots were placed in the glasshouse in randomized pots. They were watered overhead 24 hours after treatment and mat watered thereafter. After treatment the plants were arranged in the glasshouse in a randomized block design. Visual assessment of percentage reduction in green area was made 17 days after treatment in comparison with untreated plants.

The growth stage of the plants when treated was as follows:

| Bayer Code | Species | Growth Stage at Treatment |
|---|---|---|
| GALAP | Galium aparine | 2 whorls, branching |
| VERHE | Veronica hederifolia | 2–4 leaves |
| VIOAR | Viola arvensis | 2 leaves |

The levels of control observed for each mixture treatment were compared with expected values calculated from the response of plants to each component compound applied alone (Colby 1967). Where possible, effective dose (ED) rates giving 50% or 90% control were calculated using log/probit analysis (in the case of Galium aparine ED50 values were calculated; in the cases of Veronica hederifolia and Viola arvensis ED90 values were calculated). Isoboles were then constructed to illustrate the nature of the interaction (Tammes 1964). The expected values are shown in parentheses in the Table that follows, as are the respective ED50 and ED90 values. In each case the rate is expressed in g/ha:

TABLE D1

| Compound | Rate | GALAP | VERHE | VIOAR |
|---|---|---|---|---|
| A | 0.5 | 3 | 15 | 0 |
| A | 1 | 8 | 11 | 10 |
| A | 2 | 8 | 16 | 23 |
| A | 4 | 13 | 45 | 25 |
| A | 8 | 33 | 60 | 53 |
| A | 16 | 55 | 74 | 48 |
| A | 31 | 63 | 90 | 58 |
| A | 63 | 73 | 99 | 85 |
| A | 125 | 80 | 98 | 95 |
| | ED50/90 | 20 | 25 | 83 |
| Brom | 8 | 25 | 6 | 35 |
| Brom | 16 | 10 | 11 | 33 |
| Brom | 31 | 43 | 18 | 35 |
| Brom | 63 | 58 | 13 | 60 |
| Brom | 125 | 70 | 43 | 65 |
| Brom | 250 | 90 | 91 | 95 |
| | ED50/90 | 67 | 283 | 214 |
| A + Brom | 0.5 + 8 | 5 (27) | 9 (20) | 45 (35) |
| A + Brom | 1 + 8 | 8 (31) | 24 (16) | 34 (42) |
| A + Brom | 2 + 8 | 28 (31) | 55 (21) | 63 (50) |
| A + Brom | 4 + 8 | 33 (35) | 58 (48) | 63 (51) |
| A + Brom | 8 + 8 | 28 (50) | 78 (62) | 85 (69) |
| A + Brom | 16 + 8 | 43 (66) | 90 (76) | 95 (66) |
| A + Brom | 31 + 8 | 70 (72) | 96 (91) | 96 (82) |
| A + Brom | 63 + 8 | 70 (80) | 98 (99) | 100 (90) |
| | ED50/90 | 15 | 9 | 12 |
| A + Brom | 0.5 + 16 | 13 (13) | 53 (24) | 50 (33) |
| A + Brom | 1 + 16 | 18 (17) | 70 (21) | 48 (40) |
| A + Brom | 2 + 16 | 38 (17) | 78 (25) | 63 (48) |
| A + Brom | 4 + 16 | 35 (22) | 83 (51) | 68 (50) |
| A + Brom | 8 + 16 | 58 (40) | 90 (64) | 96 (69) |
| A + Brom | 16 + 16 | 65 (60) | 96 (77) | 100 (65) |
| A + Brom | 31 + 16 | 70 (67) | 95 (91) | 99 (82) |
| A + Brom | 63 + 16 | 80 (76) | 95 (99) | 100 (90) |
| | ED50/90 | 7 | 9 | 5 |
| A + Brom | 0.5 + 31 | 30 (45) | 65 (30) | 65 (35) |
| A + Brom | 1 + 31 | 45 (48) | 70 (27) | 75 (42) |
| A + Brom | 2 + 31 | 48 (48) | 78 (31) | 89 (50) |
| A + Brom | 4 + 31 | 60 (50) | 89 (55) | 93 (51) |
| A + Brom | 8 + 31 | 60 (62) | 90 (67) | 99 (69) |
| A + Brom | 16 + 31 | 73 (74) | 91 (79) | 100 (66) |
| A + Brom | 31 + 31 | 83 (79) | 95 (92) | 99 (82) |
| A + Brom | 63 + 31 | 83 (85) | 96 (99) | 98 (90) |
| | ED50/90 | 2 | 17 | 5 |
| A + Brom | 0.5 + 63 | 50 (59) | 80 (26) | 88 (60) |
| A + Brom | 1 + 63 | 63 (61) | 83 (23) | 78 (64) |
| A + Brom | 2 + 63 | 63 (61) | 88 (27) | 90 (69) |
| A + Brom | 4 + 63 | 70 (63) | 78 (52) | 98 (70) |
| A + Brom | 8 + 63 | 83 (72) | 90 (65) | 99 (81) |
| A + Brom | 16 + 63 | 83 (81) | 96 (77) | 100 (79) |
| A + Brom | 31 + 63 | 91 (84) | 96 (91) | 100 (89) |
| A + Brom | 63 + 63 | 95 (89) | 99 (99) | 100 (94) |
| | ED50/90 | 1 | 5 | 2 |

Figure 2:
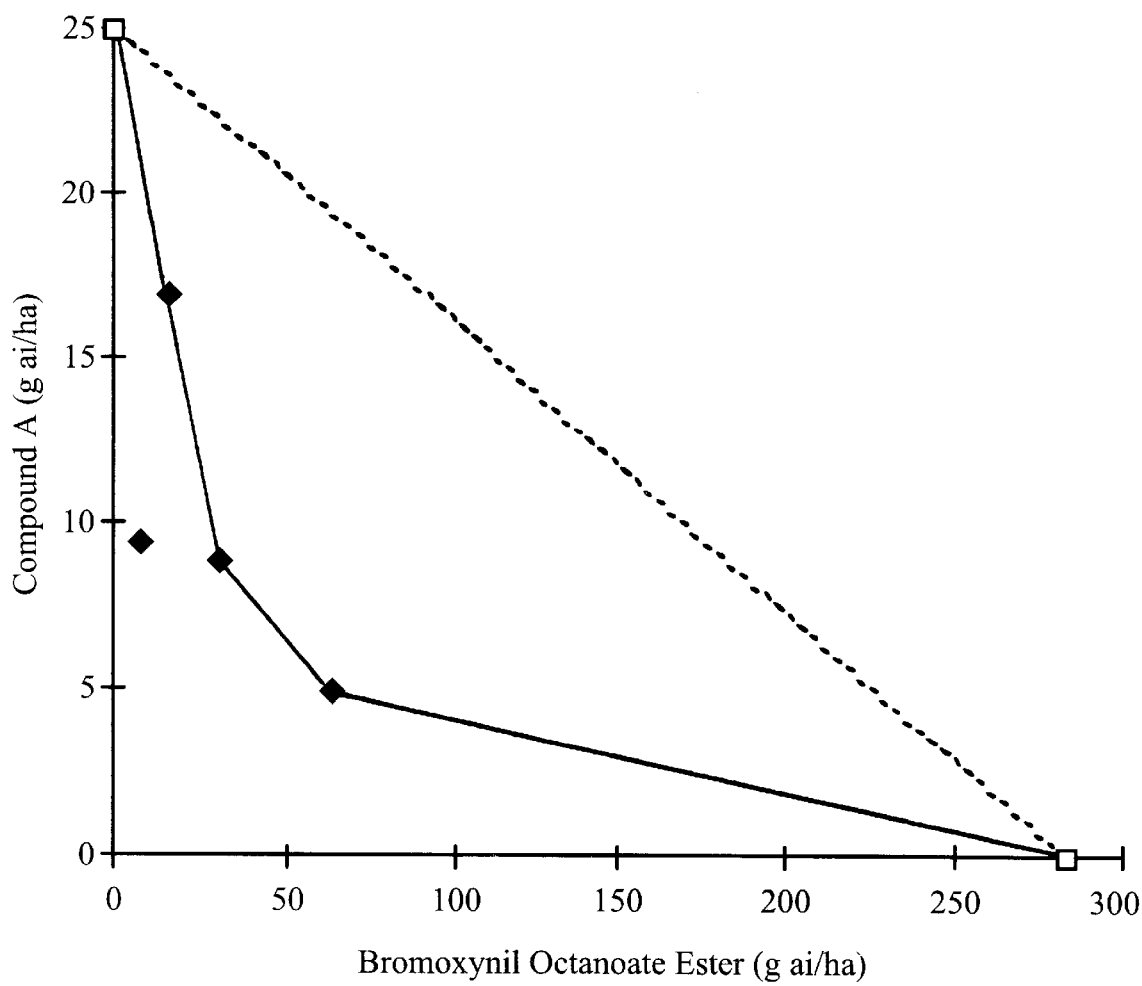
FIG. 2 is an ED90 plot calculated from observed values (-●-) and a corresponding plot of expected additive values (dashed line) for the mixtures of Compound A with bromoxynil against the weed species *Veronica hederifolia*.
Figure 3:
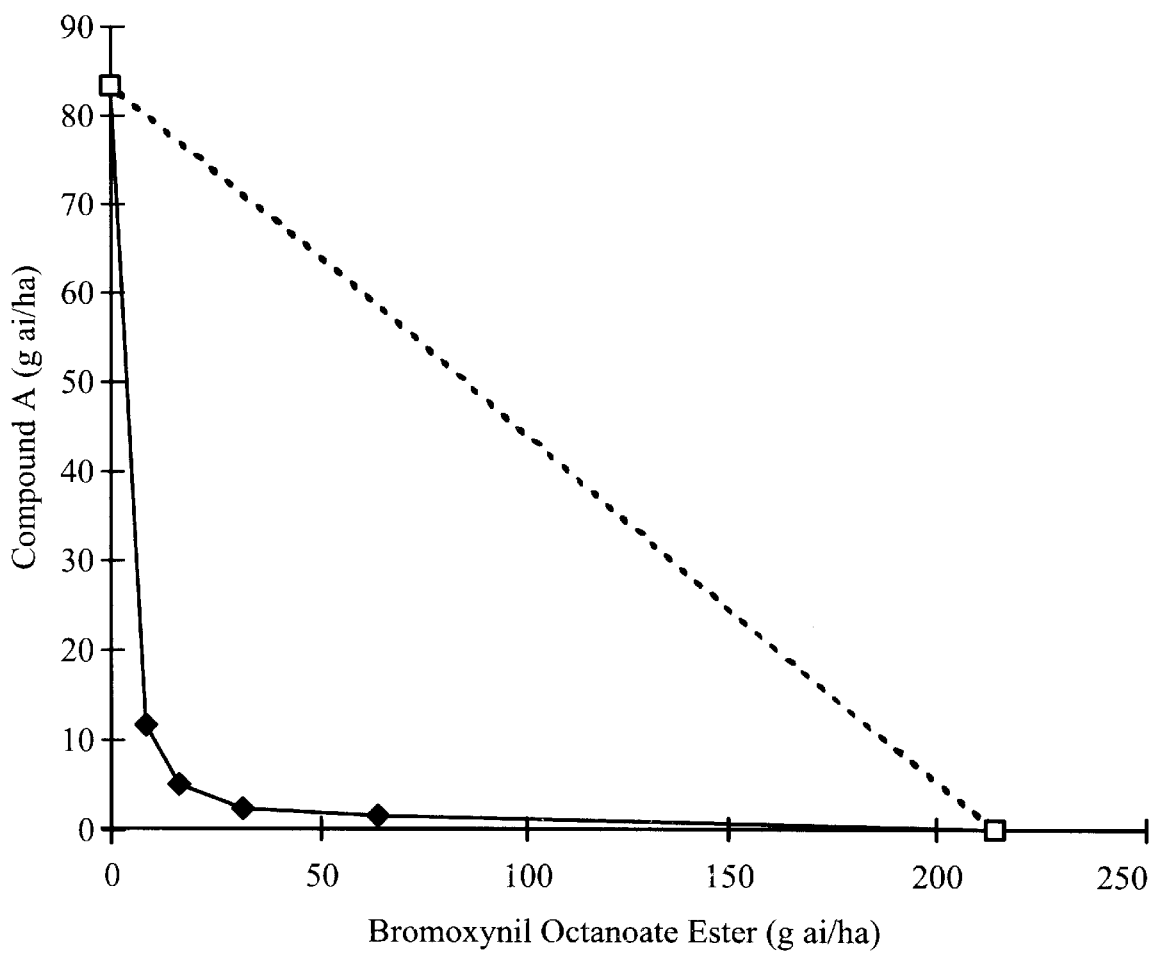
FIG. 3 is an ED90 plot calculated from observed values (-●-) and a corresponding plot of expected additive values (dashed line) for the mixtures of Compound A with bromoxynil against the weed species *Viola arvensis*.

The isoboles produced from the data in Table D1, shown in FIGS. 1 to 3 hereafter, were clearly type III curves (Tammes, op. cit., Page 75, FIG. 2), characteristic of synergism.

EXAMPLE 5

The following field trials were conducted in Mereville, France (referred to below as location FR1; loamy-clay-sand soil); Seville, Spain (referred to below as location ES1; sandy-loam soil); Essex, England (referred to below as location UK1; sandy-loam soil); and Alzonne, France (referred to below as location FR2; clay-loam soil). Compound A (as a 75% by weight wettable granule) and ioxynil (as the octanoate ester, an emulsifiable concentrate sold as "Totril"™) or bromoxynil (as the octanoate ester, formulated as a 20% wettable powder) were applied either alone or in tank mix combination in the early spring post emergence to winter-germinating weed species, and the percentage phytotoxicity in each weed species was assessed by comparison with an untreated control 48 days after treatment (DAT) at location FR1; 55 DAT at location ES1; 56 DAT at location UK1; and 77 DAT at location FR2.

The results were as follows with the figures in parentheses indicating the expected control according to the Colby formula (note 'A.I.' means active ingredient; 'Brom' means bromoxynil as described above).

soil); Compound A (formulated as a 75% wettable granule) and H (formulated as a 50% wettable powder) and bromoxynil (octanoate ester, formulated as a 20% wettable powder) were applied either alone or as a tank mix early-post emergence to spring-germinating weed species in a spring-sown crop, and the percentage phytotoxicity in each weed species was compared by comparison with an untreated control 35 or 36 days after treatment. The results are shown in the Table F1 below, with the figures in parentheses

TABLE E1

Results

| | | Weed Species | | | | | | |
|---|---|---|---|---|---|---|---|---|
| A.I. | Location Dose (g/ha) | FR1 STEME | FR1 VERHE | ES1 MATCH | ES1 STEME | ES1 FUMOF | UK1 STEME | UK1 VERHE |
| Cpd A | 22.5 | 83 | 80 | 0 | 20 | 20 | 0 | 0 |
| Brom | 120 | 90 | 30 | 20 | 0 | 0 | 0 | 0 |
| Cpd A + Brom | 22.5 + 120 | 90(98) | 90(86) | 15(20) | 40(20) | 55(20) | 37(0) | 53(0) |
| Ioxynil | 120 | 70 | 60 | 30 | 20 | 35 | 0 | 0 |
| Cpd A + Ioxynil | 22.5 + 120 | 98(95) | 100(92) | 35(30) | 25(36) | 40(48) | 53(0) | 53(0) |

| | | Weed Species | | | | | | | |
|---|---|---|---|---|---|---|---|---|---|
| A.I. | Location Dose (g/ha) | UK1 MATSS | FR2 STEME | FR2 VERHE | FR2 MATCH | FR2 PAPRH | FR2 SINAR | FR2 VERHE | GALAP |
| Cpd A | 22.5 | 0 | 15 | 30 | 40 | 15 | 65 | 25 | 5 |
| Brom | 120 | 83 | 35 | 25 | 90 | 50 | 80 | 40 | 23 |
| Cpd A + Brom | 22.5 + 120 | 43(83) | 35(45) | 35(48) | 93(94) | 45(58) | 97(93) | 40(55) | 10(27) |
| Ioxynil | 120 | 0 | 45 | 33 | 93 | 35 | 92 | 40 | 38 |
| Cpd A + Ioxynil | 22.5 + 120 | 37(0) | 60(53) | 60(53) | 93(96) | 45(45) | 97(97) | 94(55) | 50(41) |

EXAMPLE 6

The following field trials were conducted in Volga, U.S.A. (referred to below as location US1; silt-loam soil); and Indiana, U.S.A. (referred to below as location US2; silt-loam indicating the expected control according to the Colby formula (note 'A.I.' means active ingredient; 'Brom' means bromoxynil as described above).

TABLE F1

| A.I. | Location Dose (g/ha) | US1 ABUTH | US2 ABUTH | US1 AMARE | US2 AMARE | US1 AMATA | US1 ECHCG | US2 ECHCG |
|---|---|---|---|---|---|---|---|---|
| Brom | 60 | 10 | 0 | 8 | 28 | 10 | 0 | 0 |
| Brom | 120 | 73 | 85 | 60 | 93 | 53 | 0 | 20 |
| Cpd A | 15 | 65 | 25 | 30 | 0 | 58 | 43 | 45 |
| Brom + Cpd A | 60 + 15 | 100(69) | 100(25) | 100(36) | 100(28) | 97(62) | 97(43) | 55(45) |
| Brom + Cpd A | 120 + 15 | 100(91) | 100(89) | 90(72) | 98(93) | 94(80) | 98(43) | 95(56) |
| Cpd H | 25 | 43 | 92 | 10 | 0 | 8 | 0 | 25 |
| Brom + Cpd H | 60 + 25 | 100(49) | 100(92) | 99(17) | 100(28) | 99(17) | 93(0) | 90(25) |
| Brom + Cpd H | 120 + 25 | 100(43) | 100(91) | 100(10) | 100(0) | 99(8) | 92(0) | 95(25) |

| A.I. | Location Dose (g/ha) | US1 HELAN | US2 PANMI | US1 SETFA | US2 SETFA | US1 SETLU | US2 SETLU | US1 SORVU | US2 SORVU |
|---|---|---|---|---|---|---|---|---|---|
| Brom | 60 | 18 | 0 | 0 | 0 | 0 | 0 | 0 | 0 |
| Brom | 120 | 73 | 0 | 0 | 0 | 0 | 0 | 0 | 0 |
| Cpd A | 15 | 30 | 0 | 0 | 0 | 28 | 0 | 10 | 0 |
| Brom + Cpd A | 60 + 15 | 100(43) | 10(0) | 10(0) | 35(0) | 67(28) | 0(0) | 0(10) | 0(0) |
| Brom + Cpd A | 120 + 15 | 65(81) | 0(0) | 53(0) | 5(0) | 95(28) | 0(0) | 23(10) | 0(0) |

TABLE F1-continued

| | | | | | | | | | |
|---|---|---|---|---|---|---|---|---|---|
| Cpd H | 25 | 20 | 0 | 0 | 20 | 0 | 13 | 8 | 0 |
| Brom + Cpd H | 60 + 25 | 85(34) | 0(0) | 15(0) | 50(20) | 65(0) | 0(13) | 23(8) | 0(0) |
| Brom + Cpd H | 120 + 25 | 80(20) | 0(0) | 5(0) | 60(20) | 71(0) | 18(13) | 0(8) | 0(0) |

According to a further feature of the present invention, there are provided herbicidal compositions comprising:
(a) a 4-benzoylisoxazole herbicide; and
(b) bromoxynil or ioxynil, an agriculturally acceptable salt or ester thereof or a mixture thereof, preferably a metal or amine salt or an ester thereof with an alkanoic acid having from 2 to 10 carbon atoms;
in association with, and preferably homogeneously dispersed in, one or more compatible herbicidally acceptable diluents or carriers and/or surface-active agents (i.e. diluents or carriers or surface-active agents of the type generally acceptable in the art as being suitable for use in herbicidal compositions and which are compatible with bromoxynil and ioxynil and 4-benzoylisoxazole herbicides). The term "homogeneously dispersed" is used to include compositions in which the HBN herbicide and 4-benzoylisoxazole herbicide are dissolved in the other components. The term "herbicidal composition" is used in a broad sense to include not only compositions which are ready for use as herbicides but also concentrates which must be diluted before use.

The compositions preferably comprise 4-benzoylisoxazole herbicide and HBN herbicide in proportions of from about 1:120 to about 16.7:1, preferably from about 1:10 to about 5:1 wt/wt of (a):(b).

Preferably, the compositions contain from about 0.05 to about 90% by weight of HBN herbicide and 4-benzoylisoxazole derivative(s).

The herbicidal compositions may contain both a diluent or carrier and a surface-active (e.g. wetting, dispersing, or emulsifying) agent. Surface-active agents which may be present in herbicidal compositions of the present invention may be of the ionic or non-ionic types, for example sulforicinoleates, products based on condensates of ethylene oxide with nonyl- or octyl-phenols, or carboxylic acid esters of anhydrosorbitols which have been rendered soluble by etherification of the free hydroxy groups by condensation with ethylene oxide, alkali and alkaline earth metal salts or sulfuric acid esters and sulfonic acids such as dinonyl- and dioctyl-sodium sulfono-succinates and alkali and alkaline earth metal salts of high molecular weight sulfonic acid derivatives such as sodium and calcium lignosulfonates. Examples of suitable solid diluents or carriers are aluminum silicate, talc, calcined magnesia, kieselguhr, tricalcium phosphate, powdered cork, absorbent carbon black and clays such as kaolin and bentonite. The solid compositions (which may take the form of dusts, granules or wettable powders) are preferably prepared by grinding the HBN herbicides, e.g. bromoxynil, and the 4-benzoylisoxazole derivative with solid diluents or by impregnating the solid diluents or carriers with solutions of HBN herbicide and 4-benzoylisoxazole derivative in volatile solvents, evaporating the solvents and, if necessary, grinding the products so as to obtain powders. Granular formulations may be prepared by absorbing the HBN herbicide and the 4-benzoylisoxazole derivative (dissolved in volatile solvents) onto the solid diluents or carriers in granular form and evaporating the solvents, or by granulating compositions in powder form obtained as described above. Solid herbicidal compositions, particularly wettable powders, may contain wetting or dispersing agents (for example, of the types described above), which may also, when solid, serve as diluents or carriers.

Liquid compositions according to the invention may take the form of aqueous-organic solutions, suspensions and emulsions which may incorporate a surface-active agent. Suitable liquid diluents for incorporation in the liquid compositions include water, acetophenone, cyclohexanone, isophorone, toluene, xylene and mineral, animal and vegetable oils (and mixtures of these diluents). Surface-active agents, which may be present in the liquid compositions, may be ionic or non-ionic (for example of the types described above) and may, when liquid, also serve as diluents or carriers.

Wettable powders and liquid compositions in the form of concentrates may be diluted with water or other suitable diluents, for example, mineral or vegetable oils, particularly in the case of liquid concentrates in which the diluent or carrier is an oil, to give compositions ready for use. When desired, liquid compositions of HBN herbicide and 4-benzoylisoxazole derivative may be used in the form of self-emulsifying concentrates containing the active substances dissolved in the emulsifying agents compatible with the active substances, the simple addition of water to such concentrates producing compositions ready for use.

Liquid concentrates in which the diluent or carrier is an oil may be used without further dilution using the electrostatic spray technique.

Herbicidal compositions according to the present invention may also contain, if desired, conventional adjuvants such as adhesives, protective colloids, thickeners, penetrating agents, stabilizers, sequestering agents, anti-caking agents, coloring agents and corrosion inhibitors. These adjuvants may also serve as carriers or diluents.

Preferred herbicidal compositions according to the present invention are in the form of aqueous suspension concentrates; wettable powders; liquid water soluble concentrates; liquid emulsifiable suspension concentrates; granules or emulsifiable concentrates. Where Compound F is present in the herbicidal composition, preferably the composition is in the form of an emulsifiable concentrate.

In addition, the compositions may be provided in the form of a gel. This is particularly useful where the composition is intended for packaging in a water-soluble bag, for example, as described in European Patent Publication Nos. 0577702 and 0608340, and U.S. Pat. Nos. 5,222,595; 5,224,601; 5,351,831; and 5,323,906. All of these documents are incorporated by reference herein in their entireties and relied upon.

The processes described in European Patent Publication Nos. 0418175, 0487357, 0527036 and 0560482 may be used to prepare the compounds of formula (I).

Herbicidal compositions according to the present invention may also comprise the HBN herbicide and 4-benzoylisoxazole herbicide in association with, and preferably homogeneously dispersed in, one or more other pesticidally active compounds and, if desired, one or more compatible pesticidally acceptable diluents or carriers, surface-active agents or conventional adjuvants as hereinbefore described.

Pesticidally active compounds and other biologically active materials which may be included in, or used in conjunction with, the herbicidal compositions of the present invention, for example, those hereinbefore mentioned, and which are acids, may, if desired, be utilized in the form of conventional derivatives, for example, alkali metal and amine salts and esters. Preferably, the additional biologically active material is a herbicide.

The following Examples illustrate compositions according to the invention. In the description that follows the following trademarks appear: Tergitol, Atlox, Aerosol OT/B, Solvesso, Arylan, Synperonic.

EXAMPLE C1

The following formulation was prepared:

| | |
|---|---|
| Compound F | 20% |
| Bromoxynil | 20% |
| Tergitol; XD | 4% |
| Atlox G3300B | 5% |
| Sodium lauryl sulphate | 2% |
| Aerosol OT/B | 0.5% |
| Sodium acetate | 0.4% |
| Solvesso 200 | to 100% |

This was processed to subsequently yield a gel formulation according to methods known in the art.

EXAMPLE C2

An emulsifiable concentrate was prepared using the following ingredients:

| | |
|---|---|
| Compound F | 20% |
| Bromoxynil | 45% |
| Arylan CA | 4% |
| Synperonic NPE1800 | 4% |
| Solvesso 200 | to 100% | by dissolving the active ingredients in Solvesso 200 solvent at 50° C. The mixture was cooled, the remaining components were then added and the formulation was made up to volume with Solvesso 200 solvent.

By proceeding in a similar manner the following emulsifiable concentrates were prepared:

EXAMPLE C3

| | |
|---|---|
| Compound F | 20% |
| Bromoxynil | 10% |
| Arylan CA | 4% |
| Synperonic NPE1800 | 4% |
| Solvesso 200 | to 100% |

EXAMPLE C4

| | |
|---|---|
| Compound F | 6% |
| Bromoxynil | 42% |
| Arylan CA | 4% |
| Synperonic NPE1800 | 4% |
| Solvesso 200 | to 100% |

EXAMPLE C5

| | |
|---|---|
| Compound F | 6% |
| Bromoxynil | 12% |
| Arylan CA | 4% |
| Synperonic NPE1800 | 4% |
| Solvesso 200 | to 100% |

According to a further feature of the present invention, there is provided a product comprising:

(a) a 4-benzoylisoxazole herbicide; and (b) bromoxynil or ioxynil, an agriculturally acceptable salt or ester thereof or a mixture thereof, preferably a metal or amine salt or an ester thereof with an alkanoic acid containing from 2 to 10 carbon atoms;

as a combined preparation for simultaneous, separate or sequential use, for example, in controlling the growth of weeds at a locus, e.g. crop locus.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method for controlling the growth of weeds at a locus which comprises applying to said locus a synergistic herbicidally effective amount of:

(a) a 4-benzoylisoxazole herbicide having the formula:

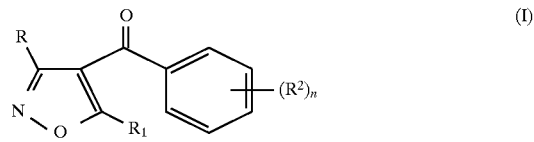

wherein:
R is hydrogen or —$CO_2R^3$;
$R^1$ is cyclopropyl;
$R^2$ is selected from the group consisting of halogen, —$S(O)_p$Me, $C_{1-6}$ alkyl and $C_{1-6}$ haloalkyl;
n is two or three;
p is zero, one or two; and
$R^3$ is $C_{1-4}$ alkyl; and (b) bromoxynil, which is 3,5-dibromo-4-hydroxybenzonitrile, or an agriculturally acceptable salt or ester thereof.

2. A method according to claim 1, wherein the compound of formula (I) is ethyl 5-cyclopropyl-4-(2-methylsulfonyl-4-trifluoromethyl)benzoylisoxazolecarboxylate.

3. A method according to claim 1, comprising applying (a) at a rate of from about 5 g to about 500 g per hectare and (b) at a rate of from about 30 g to about 600 g acid equivalent per hectare.

4. A method according to claim 1, wherein bromoxynil is in the form of an agriculturally acceptable metal or amine salt, or an agriculturally acceptable ester thereof with an alkanoic acid having from 2 to 10 carbon atoms.

5. A method according to claim 1, wherein, in formula (I), n is three and the groups $(R^2)_n$ occupy the 2, 3 and 4-positions of the benzoyl ring; or wherein n is two and the groups $(R^2)_n$ occupy the 2 and 4-positions of the benzoyl ring.

6. A method according to claim 1, wherein, in formula (I), one of the groups $R^2$ is —S(O)$_p$Me.

7. A method according to claim 1, wherein the compound of formula (I) is 5-cyclopropyl-4-(2-methylsulfonyl-4-trifluoromethyl)benzoylisoxazole.

8. A method according to claim 1, wherein the compound of formula (I) is ethyl 3-[5-cyclopropyl-4-(3,4-dichloro-2-methylsulfenyl)benzoylisoxazole]carboxylate.

9. A method according to claim 1, comprising applying (a) and (b) post-emergence.

10. A method according to claim 1, wherein the locus is an area used, or to be used, for growing maize or winter cereals.

11. A method according to claim 1, wherein the compound of formula (I) is 5-cyclopropyl-4-(2-methylsulfonyl-4-trifluoromethyl)benzoylisoxazole and (b) is bromoxynil octanoate ester.

12. A herbicidal composition comprising a synergistic herbicidally effective amount of:

(a) a 4-benzoylisoxazole having the formula:

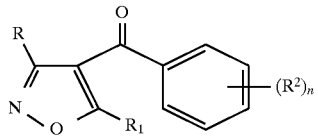

wherein:
R is hydrogen or —CO$_2$R$^3$;
R$^1$ is cyclopropyl;
R$^2$ is selected from the group consisting of halogen, —S(O)$_p$Me, C$_{1-6}$ alkyl and C$_{1-6}$ haloalkyl;
n is two or three;
p is zero, one or two; and
R$^3$ is C$_{1-4}$ alkyl; and (b) bromoxynil, which is 3,5-dibromo-4-hydroxybenzonitrile, or an agriculturally acceptable salt or ester thereof;
and at least one member selected from the group consisting of herbicidally acceptable carriers and herbicidally acceptable surface-active agents.

13. A composition according to claim 12, wherein bromoxynil is in the form of an agriculturally acceptable metal or amine salt, or an agriculturally acceptable ester thereof with an alkanoic acid having from 2 to 10 carbon atoms.

14. A composition according to claim 12, comprising from about 1:120 to about 16.7:1 wt/wt of (a):(b) acid equivalent.

15. A composition according to claim 12, wherein the compound of formula (I) is 5-cyclopropyl-4-(2-methylsulfonyl-4-trifluoromethyl)benzoylisoxazole and (b) is bromoxynil octanoate ester.

16. A herbicidal composition comprising a synergistic herbicidally effective amount of (a) 5-cyclopropyl-4-(2-methylsulfonyl-4-trifluoromethyl)benzoylisoxazole; and (b) bromoxynil, which is 3,5-dibromo-4-hydroxybenzonitrile, an agriculturally acceptable salt or ester thereof;

and at least one member selected from the group consisting of herbicidally acceptable diluents and herbicidally acceptable surface-active agents.

17. A product comprising a synergistic herbicidally effective amount of:

(a) a 4-benzoylisoxazole herbicide having the formula:

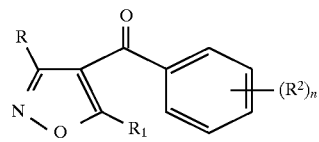

wherein:
R is hydrogen or —CO$_2$R$^3$;
R$^1$ is cyclopropyl;
R$^2$ is selected from the group consisting of halogen, S(O)$_p$Me, C$_{1-6}$ alkyl and C$_{1-6}$ haloalkyl;
n is two or three;
p is zero, one or two; and
R$^3$ is C$_{1-4}$ alkyl; and (b) bromoxynil, which is 3,5-dibromo-4-hydroxybenzonitrile, or an agriculturally acceptable salt or ester thereof;

as a combined preparation for simultaneous, separate or sequential application at a locus.

18. A product according to claim 17, wherein the compound of formula (I) is 5-cyclopropyl-4-(2-methylsulfonyl-4-trifluoromethyl)benzoylisoxazole and (b) is bromoxynil octanoate ester.

* * * * *